(12) United States Patent
Verreydt et al.

(10) Patent No.: US 10,495,503 B2
(45) Date of Patent: Dec. 3, 2019

(54) DEVICE FOR DETERMINING MASS TRANSPORT OF A FLUID AND A SUBSTANCE DISSOLVED IN THE FLUID

(71) Applicants: VITO NV (VLAAMSE INSTELLING VOOR TECHNOLOGISCH ONDERZOEK NV), Mol (BE); UNIVERSITEIT ANTWERPEN, Antwerp (BE)

(72) Inventors: Goedele Verreydt, Rijmenam (BE); Simon De Meulenaer, Bonheiden (BE); Filip Meesters, Gravenwezel (BE)

(73) Assignees: VITO NV (VLAAMSE INSTELLING VOOR TECHNOLOGISCH ONDERZOEK NV), Mol (BE); UNIVERSITEIT ANTWERPEN, Antwerp (BE)

( * ) Notice: Subject to any disclaimer, the term of this patent is extended or adjusted under 35 U.S.C. 154(b) by 52 days.

(21) Appl. No.: 15/739,415

(22) PCT Filed: Jun. 17, 2016

(86) PCT No.: PCT/IB2016/053620
§ 371 (c)(1),
(2) Date: Dec. 22, 2017

(87) PCT Pub. No.: WO2016/207769
PCT Pub. Date: Dec. 29, 2016

(65) Prior Publication Data
US 2018/0180457 A1 Jun. 28, 2018

(30) Foreign Application Priority Data
Jun. 25, 2015 (BE) ................................... 2015/5391

(51) Int. Cl.
| | | |
|---|---|---|
| G01F 1/708 | (2006.01) | |
| G01N 1/10 | (2006.01) | |
| G01F 1/704 | (2006.01) | |
| G01N 33/18 | (2006.01) | |

(Continued)

(52) U.S. Cl.
CPC .............. *G01F 1/708* (2013.01); *G01F 1/704* (2013.01); *G01F 1/74* (2013.01); *G01N 1/10* (2013.01); *G01N 1/12* (2013.01); *G01N 33/1886* (2013.01)

(58) Field of Classification Search
CPC ............. G01F 1/704; G01F 1/74; G01F 1/708
See application file for complete search history.

(56) References Cited

U.S. PATENT DOCUMENTS 5,996,423 A 12/1999 Baghel et al.
7,325,443 B2 * 2/2008 De Jonge ................ G01F 1/704
73/61.72

(Continued)

FOREIGN PATENT DOCUMENTS

WO 01/33173 A1 5/2001

OTHER PUBLICATIONS

Hatfield et al., "A direct passive method for measuring water and contaminant fluxes in porous media", Contaminant Hyrdrology, Elsevier, Dec. 1, 2004, pp. 155-181, vol. 75, No. 3-4, Amsterdam, NL.

(Continued)

*Primary Examiner* — Jewel V Dowtin
(74) *Attorney, Agent, or Firm* — Kolitch Romano LLP

(57) ABSTRACT

Device for simultaneously determining a mass transport of a fluid and a mass transport of a substance dissolved in the fluid, comprising at least two cartridges filled with a porous matrix, and assembly means, configured to keep the cartridges together, characterized in that the top side and the bottom side of each cartridge are non-permeable and the side (Continued)

wall is permeable, and in that the assembly means are configured to keep the cartridges together according to a stack, in which the cartridges may be flowed through in parallel without cross-contamination.

21 Claims, 11 Drawing Sheets

(51) Int. Cl.
*G01N 1/12* (2006.01)
*G01F 1/74* (2006.01)

(56) References Cited

U.S. PATENT DOCUMENTS

| | | | |
|---|---|---|---|
| 7,451,646 B2 * | 11/2008 | Cleland | G01Q 60/30 |
| | | | 73/335.04 |
| 8,763,478 B2 * | 7/2014 | Riess | G01N 1/02 |
| | | | 73/863.21 |
| 9,709,471 B2 * | 7/2017 | Riess | G01N 1/02 |
| 2014/0209384 A1 * | 7/2014 | Hanson | E21B 47/1015 |
| | | | 175/42 |
| 2014/0290391 A1 | 10/2014 | Varhol | |

OTHER PUBLICATIONS

Annable et al., "Field-Scale Evaluation of the Passive Flux Meter for Simultaneous Measurement of Groundwater and Contaminant Fluxes", Environmental Science & Technology, Sep. 1, 2005, pp. 7194-7201, vol. 39, No. 18.

Campbell et al., "Magnitude and Directional Measures of Water and Cr(VI) Fluxes by Passive Flux Meter", Supporting Information, Sep. 6, 2006, pp. S1-S8.

Campbell et al., "Magnitude and Directional Measures of Water and Cr(VI) Fluxes by Passive Flux Meter", Environmental Science & Technology, Oct. 1, 2006, pp. 6392-6397, vol. 40, No. 20.

Klammler et al., "Concepts for measuring horizontal groundwater flow directions using the passive flux meter", Advances in Water Resources, CML Publications, Feb. 21, 2007, pp. 984-997, vol. 30, No. 4, Southampton, GB.

Sep. 1, 2016, International Search Report of the International Searching Authority from the European Patent Office in PCT/IB2016/053620, which is the international application to this U.S. application.

Sep. 1, 2016, Written Opinion of the International Searching Authority from the European Patent Office in PCT/IB2016/053620, which is the international application to this U.S. application.

\* cited by examiner

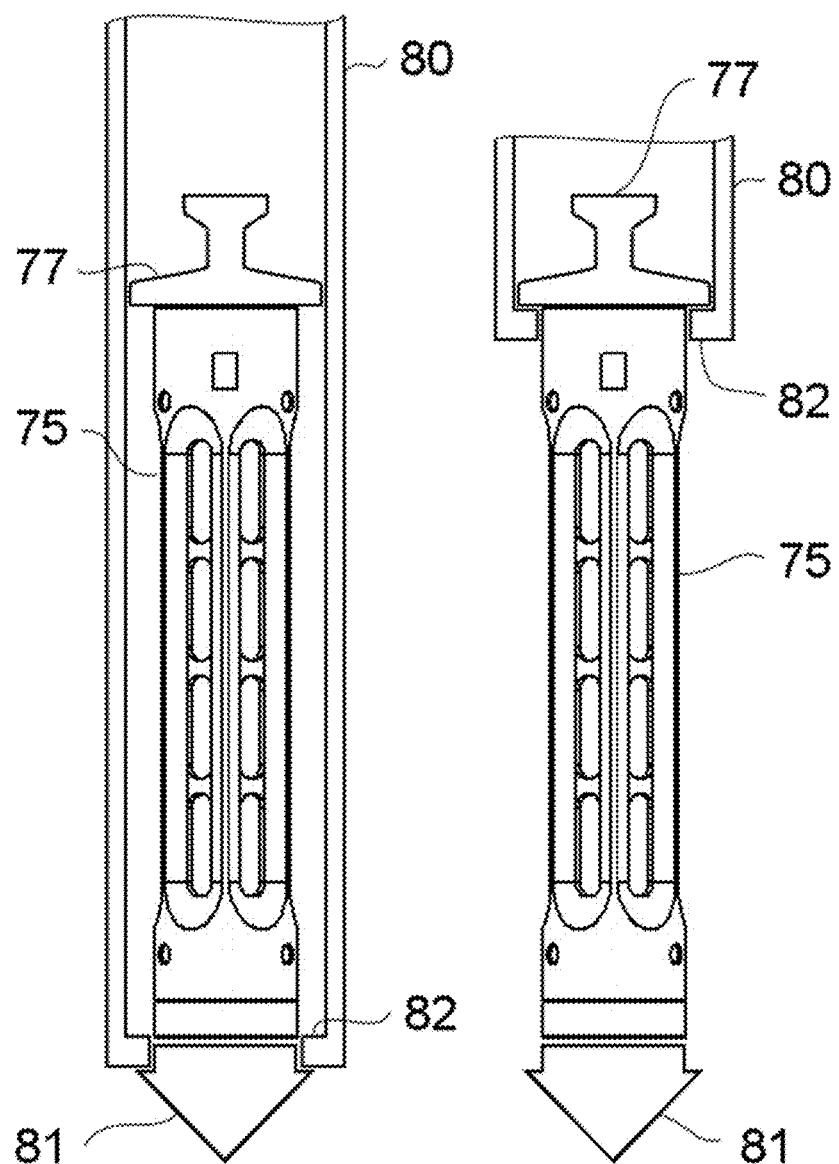

DEVICE FOR DETERMINING MASS TRANSPORT OF A FLUID AND A SUBSTANCE DISSOLVED IN THE FLUID

CROSS-REFERENCE TO RELATED APPLICATIONS

This application is a national phase application of PCT/IB2016/053620, filed Jun. 17, 2016, which claims priority to Belgium Patent Application No. 2015/5391, filed Jun. 25, 2015, each of which is hereby incorporated by reference.

BACKGROUND OF THE INVENTION

The present invention relates to a device for determining a (mass) flux of a fluid and a (mass) flux of a substance dissolved in the fluid. In particular, the fluid is a liquid, and the dissolved substance is a pollutant or a mineral. Devices in accordance with the invention are particularly suitable for measuring in underground liquid layers, such as groundwater layers.

Groundwater may be polluted by a large number of various pollutants, ranging from organic and inorganic substances, such as volatile organic hydrocarbons, mineral oil, phosphates, nitrates and pesticides, to heavy metals. For ecological and health reasons, there is growing interest in efficient risk management of groundwater which, in the case of (residual) pollution, is often the only and best available technology not incurring excessive costs. To this end, the groundwater pollution and/or groundwater fluxes have to be efficiently and accurately mapped. Only then will it be possible to correctly assess the ecological and health impact of the pollution and take any necessary action to counteract groundwater pollution and/or to limit the effects thereof.

In order to determine the quality of the groundwater, it is known to drill monitoring wells as far as the groundwater layer and to regularly take a groundwater sample via these monitoring wells using a pump and analyse it. This system only produces snapshots. As it is known that the concentration of a pollutant in the groundwater may fluctuate greatly, there is a risk that a distorted image of the groundwater pollution is obtained.

U.S. Pat. No. 5,996,423 and US 2014/0290391 describe devices for taking samples from groundwater, which are based on diffusion. These devices comprise a housing which is filled with distilled water. The housing is surrounded by a semi-permeable membrane, which is permeable to the substance to be sampled which is dissolved in the groundwater and non-permeable to the groundwater itself. The substance to be sampled will diffuse to the distilled water until an equilibrium is reached. Such systems are able to determine a time-averaged concentration of a pollutant. However, the concentration value on its own does not suffice to determine the amount of pollutant which spreads via the groundwater.

WO 01/33173 and U.S. Pat. No. 7,325,443 describe devices for determining mass transport of groundwater and of a substance dissolved in the groundwater. These devices comprise a porous matrix through which liquids can flow and which contains sorbents for the dissolved substance which is to be measured. In addition, these devices comprise so-called tracers by means of which the groundwater flux can be determined. The tracers are either impregnated in the porous matrix (WO 01/33173), or mixed therewith, or arranged separately in such a manner that they can diffuse into the porous matrix (U.S. Pat. No. 7,325,443). A drawback of such arrangements is the fact that the laboratory analysis is difficult, since mutual interference has to be taken into account. After all, the adsorption of certain pollutant molecules onto the porous matrix may affect the diffusion of the tracers and vice versa. In addition, diffusion and non-equilibrium conditions may result in a distorted image of the tracer movement.

BRIEF SUMMARY OF THE INVENTION

It is an object of the present invention to provide a device for determining mass transport of a fluid and of a substance dissolved in the fluid, which device can overcome the abovementioned drawbacks of the prior art.

It is an object of the present invention to provide a device for determining mass transport of a fluid and of a substance dissolved in the fluid, which device facilitates the laboratory analysis.

It is an object of the present invention to provide a device for determining mass transport of a fluid and of a substance dissolved in the fluid, which device is able to determine the mass transport of several substances dissolved in the fluid simultaneously and separately.

It is an object of the present invention to provide a device for determining mass transport of a fluid and of a substance dissolved in the fluid, which device is easier to use and/or more cost-efficient.

According to an aspect of the invention, a device for determining a mass transport of a fluid and of a substance dissolved in the fluid is therefore provided, as set out in the attached claims.

Devices according to aspects of the invention comprise at least two cartridges, with each of the cartridges comprising a top side, a bottom side and a side wall. The top side, bottom side and side wall define a flow chamber. The devices furthermore comprise assembly means configured to keep the cartridges together. The flow chamber of a first cartridge of the at least two cartridges is filled with a first porous matrix comprising a material composition configured to determine the mass transport of the fluid. The flow chamber of a second cartridge of the at least two cartridges is filled with a second porous matrix comprising a material composition configured to determine the mass transport of the substance dissolved in the fluid. Advantageously, the material composition of the first porous matrix and the material composition of the second porous matrix are different.

According to aspects of the invention, the top side and the bottom side of each of the at least two cartridges are non-permeable to the fluid, while the side wall of each of the cartridges is permeable to the fluid.

According to aspects of the invention, the assembly means are configured to keep the cartridges together according to a stack in which the top side of one of the at least two cartridges and the bottom side of a neighbouring cartridge of the at least two cartridges are opposite one another. In other words, such a stack is such that the top side and the bottom side of the two neighbouring cartridges overlap one another in a projection perpendicular to a face of the top side or the bottom side. Advantageously, the result thereof is that the flow chambers of the two neighbouring cartridges may be flowed through in parallel without cross-contamination.

Thus, a modular configuration is obtained, in which the porous matrix of each cartridge can be optimized individually with regard to composition and can be analysed separately after sampling. Advantageously, the assembly means allow for disassembly after use (after sampling).

A method for determining a mass transport of a fluid and, separately and simultaneously, of a mass transport of a substance dissolved in the fluid is also described in the attached claims.

BRIEF DESCRIPTION OF THE DRAWINGS

Aspects of the invention will be explained below with reference to the following figures, without being limited thereto.

FIGS. 11 and 12 show an arrangement for taking samples according to a "direct push" technique, wherein a tube according to FIG. 9A or an assembly according to FIG. 10 is used.

DETAILED DESCRIPTION OF THE INVENTION

Figure 1:
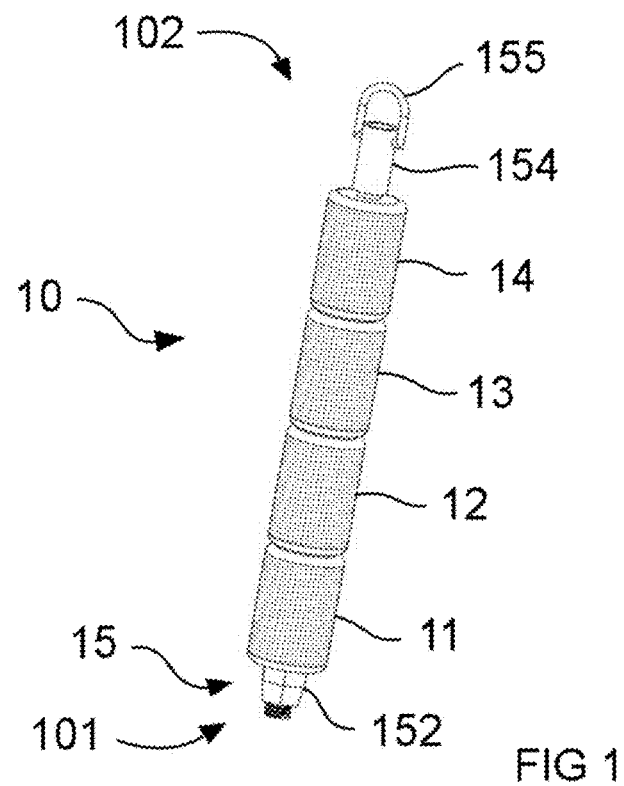
FIG. 1 shows a perspective view of a device according to aspects of the invention.

Referring to FIG. 1, a device 10 according to aspects of the invention comprises several cartridges 11-14 installed on assembly means 15 which keep the cartridges together at a fixed distance from one another.

Figure 2:
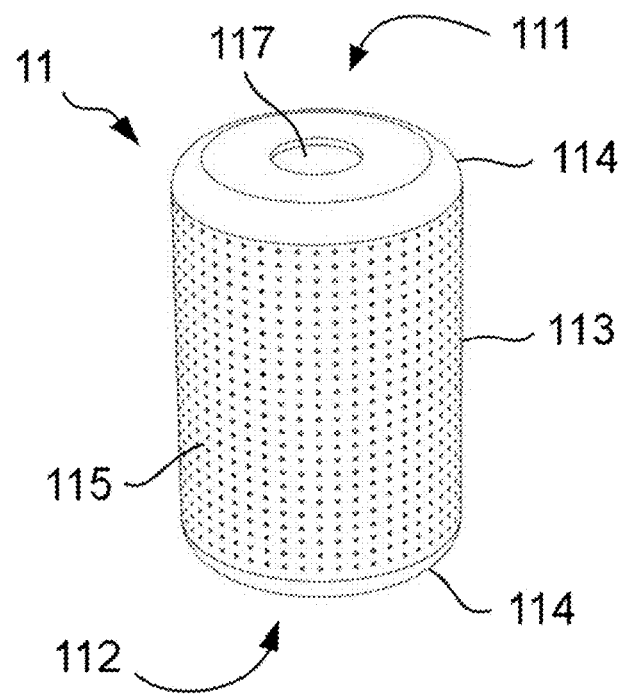
FIG. 2 shows a perspective view of a cartridge used in the device of FIG. 1.

FIG. 2 shows a cartridge 11 which is used in the device 10. The cartridge 11, which advantageously is cylindrical in shape, is delimited by a top side 111, a bottom side 112 and a side wall 113. The top side 111 and the bottom side 112 are closed off by advantageously removable lids 114, which are not permeable to the fluid in which the device will be immersed and the mass transport of which is to be determined. The side wall 113, in the shape of a cylinder sleeve, is made from a screen 115 permeable to this fluid. On the one hand, the screen 115 has to be sufficiently permeable to the fluid and, on the other hand, the mesh size of the openings in the screen 115 must not be excessively large in order not to lose the granular material situated in the cartridge 11. A mesh size having a diameter between 0.1 mm and 1 mm is usually suitable. The screen 115 may be made of metal, but, depending on its application, may also be made of a synthetic substance (e.g. a net), or a membrane.

Figure 3:
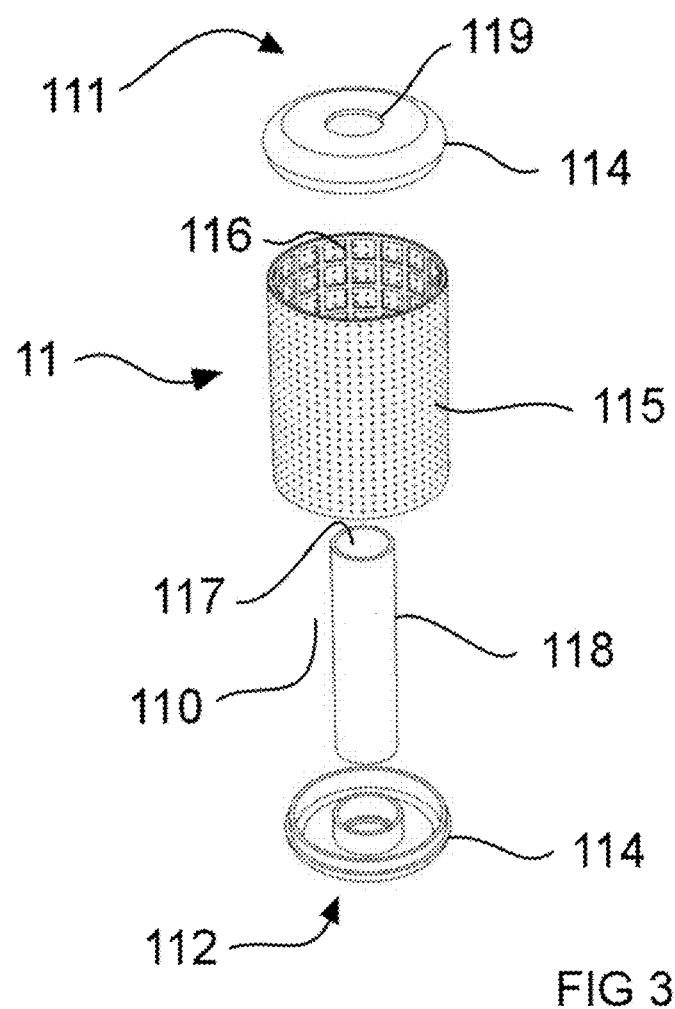
FIG. 3 shows an exploded view of the cartridge shown in FIG. 2, in which the screen has been removed.

Referring to FIG. 3, the cartridge 11 may comprise a reinforcement 116, e.g. in the form of a perforated pipe wall, which advantageously extends along the side wall 113, between the top side 111 and the bottom side 112. Advantageously, the lids 114 and the reinforcement 116 comprise connecting means to attach the lids 114 to the reinforcement 116 in an advantageously detachable way, e.g. a click-fit connection. Detachable lids make it possible to re-use the cartridges. The screen 115 may be fitted on the outer side as well as on the inner side of the reinforcement 116.

In the embodiment according to FIGS. 1 to 3, the cartridges 11-14 advantageously comprise an internal cavity 117 which extends axially between the top side 111 and the bottom side 112. This cavity 117 is advantageously formed by a central pipe 118, as is illustrated in FIG. 3. This central pipe 118 has a pipe wall impermeable to the fluid, which surrounds the cavity 117, and extends between the lids 114, each of which comprises a central passage opening 119. The central pipe 118 is connected to the central passage opening 119 of the lids in a way which is impermeable to the fluid. In other words, axial cavity 117 does not allow the fluid to access the cartridge. As will become clear below, the axial cavity 117 is necessary for installing the device 10 and can be used to assemble the cartridges.

The lids 114, the screen 115 and, optionally, the central pipe 118 define a flow chamber 110 for the fluid. This flow chamber is filled with a material which is designed to measure either a mass transport of the fluid or a mass transport of a substance dissolved in the fluid, e.g. a pollutant.

The material usually comprises a porous matrix, e.g. due to the fact that the material is a granular material, of a material composition advantageously insoluble in the fluid. The granular material may be configured to adsorb the dissolved substance, which is to be measured, in which case it is referred to as an adsorbent. Adsorbents are known and examples include cation or anion exchange resins, granular active carbon (optionally modified, e.g. by means of a surfactant), cross-linked polymer adsorbents, iron(III) hydroxide. Cation exchange resins are mainly used to adsorb inorganic pollutants and heavy metals, such as ammonium, magnesium, chromium, manganese, iron, nickel, copper, zinc, cadmium and lead. Anion exchange resins are mainly used to adsorb inorganic pollutants, such as nitrate, nitrite, phosphate and sulphate. Active carbon or polymer adsorbent can be used to adsorb volatile organic hydrocarbons, mineral oil, aromatic hydrocarbons and polyaromatic hydrocarbons. The grain sizes of the granules are usually between 0.4 mm and 2.5 mm (equivalent) diameter.

The material (the granular material) may be impregnated with a tracer, which is configured to be washed away as a result of the flow of the fluid, e.g. due to the fact that the tracer is soluble in the fluid. Examples are active carbon impregnated with alcohols, such as methanol, ethanol, 2-propanol and tert-butanol for measuring the mass transport of water. Other tracers which are leached out by the pollutants may be used for measuring the mass transport of these pollutants. It is possible to provide self-supporting tracers, which are sufficiently strong not to require adhesion to a substrate granular material. Examples are micro-encapsulated tracers and salts: inorganic salts (e.g. carbonates, hydroxides, phosphates, hydrogen phosphates, ammonium phosphates, citrates, bromides, fluorides, sulphides), organic salts (e.g. ammonium acetate). In the case of a self-supporting tracer, the matrix may consist only of the self-supporting tracer.

Figure 13:
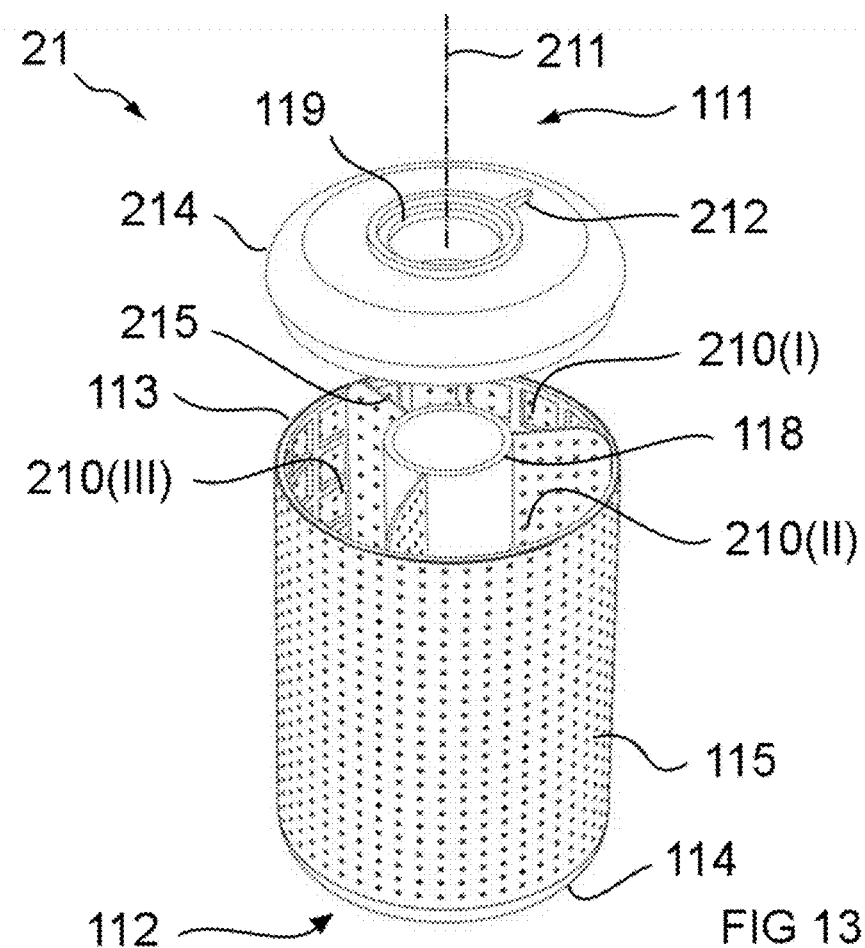
FIG. 13 shows an exploded view of a cartridge by means of which both the mass transport and the direction of the fluid flow can be determined.

The tracer may also be used to determine a flow direction. To this end, the cartridge 11 is advantageously modified to form a cartridge 21, as illustrated in FIG. 13. Cartridge 21 differs from cartridge 11 in the fact that it comprises several partitions 215, which are arranged in the flow chamber 110. The partitions 215 are parallel to an axis 211 of the cartridge, which runs from the top side 111 to the bottom side 112, and extend radially with respect to axis 211, so that the flow chamber is divided into an equivalent number of flow compartments 210(I), 210(II), 210(III). In the example, the partitions 215 extend from the wall of the central pipe 118 to the side wall 113. Advantageously, cartridge 21 comprises at least three partitions 215. The partitions 215 are advantageously permeable to the fluid, e.g. by providing perforations in the partitions. The partitions 215 are arranged in such a way that advantageously they are at different angles to the direction of flux.

The flow compartments 210(I)-(III) are filled with the granular material of the porous matrix which comprises or consists of the tracer. The partitions 215 advantageously block the (non-dissolved) granular material, so that only the portion dissolved in the fluid can migrate from one flow compartment to the other.

Advantageously, cartridge 21 comprises means to determine an orientation of the cartridge 21 with respect to an external reference system. These means may, for example, comprise a marker 212 provided on the cartridge, of which the position can be determined by an external measuring system, e.g. during lowering or raising of the cartridge into the monitoring well pipe or the borehole. Another possibility is to provide the cartridge with a lockable compass. Such compasses are known, e.g. Bouma, "Self-locking compass", Marine Geol. 1 (1964), 181-186. The orientation indicator of such a compass may be locked, for example, during lowering or raising of the cartridge in the monitoring well or the borehole. In this way, it is possible to determine, during laboratory analysis of the cartridge, which orientation the cartridge had in the flow field of the fluid. The partitions 215, possibly in combination with the orientation means, make it possible to determine the direction of the flux of the fluid with respect to the cartridge, and possibly with respect to an external reference system. A possible way of doing so is described further below.

Following assembly and possibly before a lid 114 is fitted, the cartridges may be filled with the adsorbent and/or the tracer. In case lid 114 is detachable, filling of the cartridge may be postponed until just before assembly.

According to an aspect of the invention, the device comprises at least two cartridges 11, 12, each of which is filled with a different material composition. At least one of the cartridges is filled with a porous matrix made of a material composition which is provided to measure the mass transport of the fluid, in particular groundwater. In this case, the material composition may comprise a tracer. At least one other cartridge is filled with a porous matrix made of a material composition which is provided to measure the mass transport of a pollutant. In other words, each cartridge may be provided to measure the mass transport of a specific substance. This makes it possible to optimize the material composition of the porous matrix in the cartridge for the parameter to be measured.

In addition, a third cartridge may advantageously be provided, which comprises different flow compartments 210(I), (II), (III) in order to measure the direction of the fluid flux, such as e.g. cartridge 21 from FIG. 13. In this way, each cartridge can be used to determine a different parameter, thus facilitating the laboratory analysis. Alternatively, the cartridge 21 can be used to measure both the direction and the magnitude of the mass transport (mass flux) of the fluid, so that two cartridges suffice instead of three.

Advantageously, each cartridge may be provided with a barcode, comprising an identification of the material composition in the cartridge and/or of the position in the stack. Such a barcode may be one-dimensional or two-dimensional (e.g. QR code) and may be provided on a lid.

Referring to FIG. 1, according to an aspect of the invention, the various cartridges 11-14 are advantageously stacked vertically on top of one another, so that they are separated by the lids 114. Such an arrangement makes it possible to effect a parallel flow through the cartridges by the fluid, as the impermeable lids 114 prevent fluid flow from one cartridge to another. As a result thereof, the effect of interference between different substances in the fluid on the measurement results is minimized.

Figure 4:
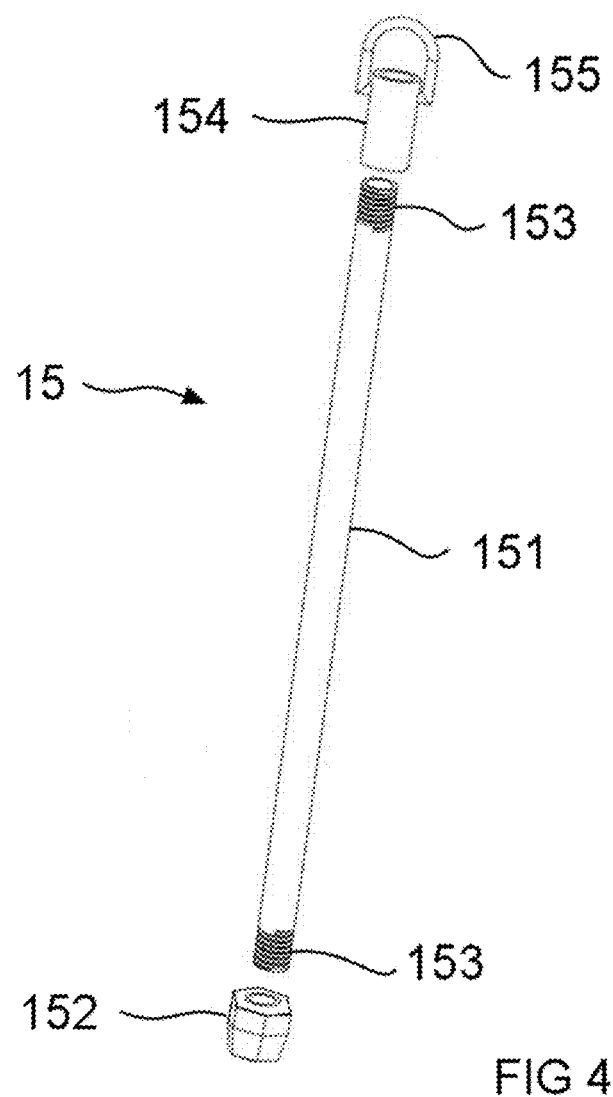
FIG. 4 shows assembly means for assembling the device of FIG. 1.

Various types of assembly means may be provided in order to hold such a stack of cartridges together. A first possibility is to directly connect the cartridges to one another, e.g. by providing the lids with screw thread or a click-fit connection. A second possibility is to attach the cartridges to a (steel) rope. A third possibility is illustrated in FIGS. 1 and 4. Here, a pipe-shaped bar 151, preferably made of metal, is provided as assembly means. Bar 151 may be provided with screw thread at both ends 153. A stop means, e.g. a nut 152, is screwed onto end 153 to serve as a stop for the cartridges, which are slid over the bar 151 by means of central pipe 118. At the other end 153 of the bar 151, a suitable stop means may also be provided, e.g. a screw cap 154. In this case, nut 152 and cap 154 have to have an outer diameter which is greater than the inner diameter of the central pipe 118 of the cartridges. Alternatively, a washer may be provided between the stop means and the cartridges. Cap 154 may be provided with an advantageously hinging eye 155 for attaching a cable (not illustrated) in order to e.g., lower the device 10 into a monitoring well pipe and raise it again. Such a cable may be attached to a lid of the monitoring well pipe or borehole, so that the device 10 remains at the correct depth.

In order to maintain cartridges 11-14 at a fixed position without the risk of being damaged during assembly, it may be advantageous to fit elastic washers, e.g. made of an elastomer, (not illustrated) between the various cartridges. These make it possible to fit the cartridges tighter together using the stop means 152 and 154.

The above-described arrangement with bar 151 has the advantage that the strength of the arrangement is not determined by the cartridges. Consequently, they do not have to have a high tensile strength, e.g. for raising the device from the subsoil. It will be clear that the flow direction of the flow through the cartridges is substantially perpendicular to the side wall.

The bar 151 and the central pipe 118 may have a non-circular cross section, e.g. polygonal, in order to prevent rotation. This may be important when the flow direction has to be determined.

The bar 151 and the stop means 152 and 154 are advantageously hollow, so that a central through-passage is obtained between the bottom end 101 and the top end 102 of the device 10, this passage being open at both ends 101 and 102. Such a through-passage facilitates the lowering and raising of the device 10 in a monitoring well pipe or borehole. Usually, the outer diameter of the device 10, e.g. the outer diameter of the cartridges 11-14, will not be much smaller than the inner diameter of the monitoring well pipe or the borehole. In such a case, the central through-passage will ensure that the fluid (water) is able to move in the monitoring well pipe or the borehole while the device 10 is moving.

The number of cartridges 11-14 which are to be stacked on top of one another not only depends on the number of pollutants to be measured, but also on the height (section length) of the groundwater layer to be analysed. By repeating cartridges, filled with the same material composition, at certain distances, it is possible to get a picture of the mass transport along an entire section of the groundwater layer.

Figure 5:
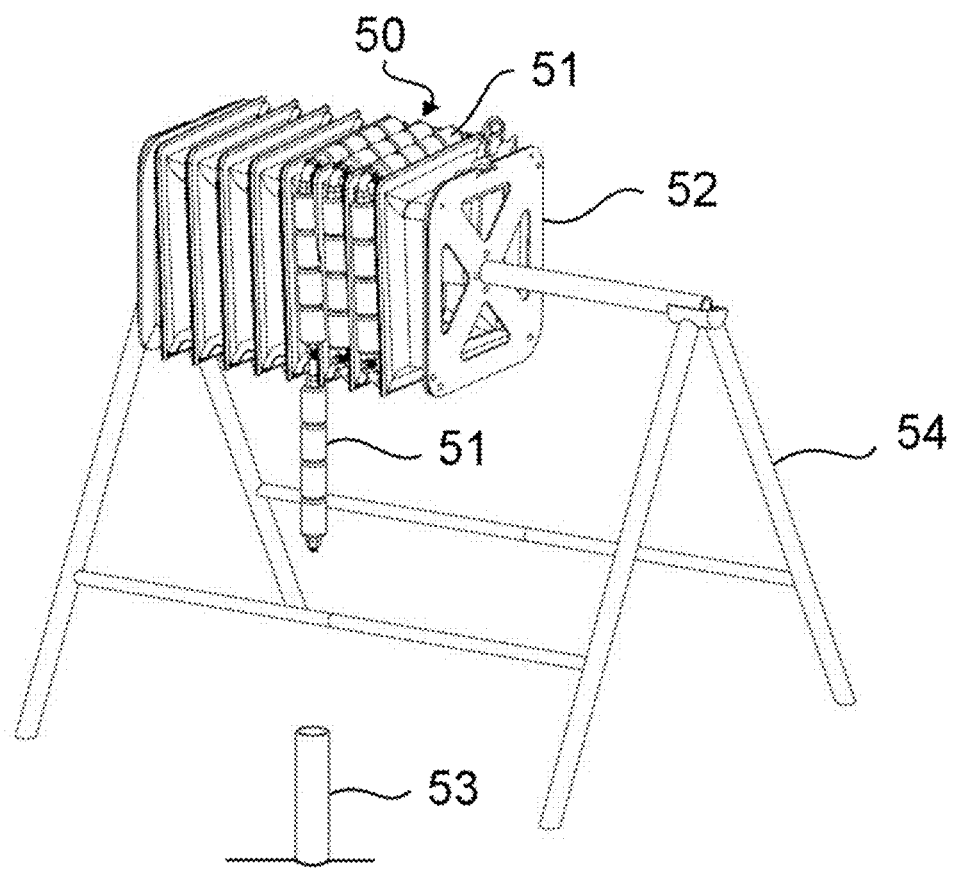
FIG. 5 shows a perspective view of a device according to aspects of the invention, which device has been divided into a plurality of identical segments and is lowered from a roll into a monitoring well pipe.
Figure 6:
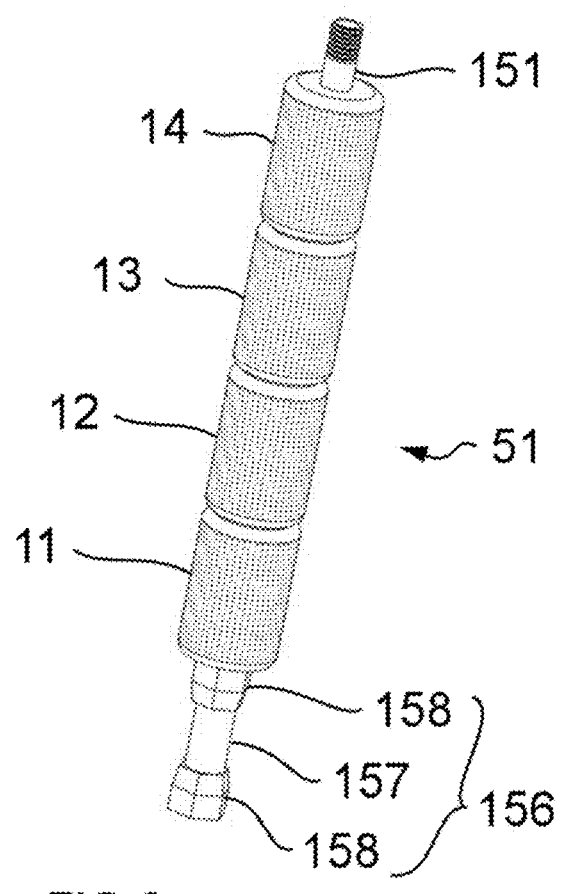
FIG. 6 shows a perspective view of a segment of the device shown in FIG. 5.

Referring to FIGS. 5 and 6, advantageously several pipe-shaped bars 151, preferably all of the same length, are used. Advantageously, several cartridges are fitted to each bar 151. The bars 151 are connected to one another via a coupling piece 156. This coupling piece 156 advantageously performs the role of stop means, e.g. by comprising a screw connection 158 at both ends. Thus, a device 50 for determining mass transport of a fluid and mass transport of a substance dissolved in the fluid is obtained, which is divided into several, advantageously identical, segments 51. Each segment 51 advantageously comprises several cartridges 11-14 which are fitted on a bar 151. A coupling piece 156 is provided at both ends of the bar 151 in order to connect successive segments 51 to one another. The segment 51 only differs from the device 10 in the stop means 152, 154. These are replaced by coupling pieces 156 between successive segments 51. A terminal cap 154 as illustrated in FIG. 1 may be provided at the top end 102 of the last (top) segment 51.

Advantageously, each segment 51 comprises an equal number of cartridges 11-14, advantageously having the same dimensions. Advantageously, corresponding cartridges of each segment 51 are filled with the same material composition of the porous matrix. In this way, an accurate analysis along a section of a groundwater layer can be performed. Alternatively, different segments 51 comprise different cartridge compositions, specifically provided for a parameter to be expected at a certain position along a vertical profile of the groundwater layer. This may in particularly occur with long profiles (long sections) in groundwater layers.

The coupling piece 156 is advantageously hollow, so that a central passage is obtained for the fluid which runs along various segments 51. Advantageously, the coupling piece 156 has a flexibility which allows successive segments 51 to tilt with respect to each other. As a result thereof, the device 50 can be rolled up onto a (square) roll 52 intended for this purpose, as is illustrated in FIG. 5. Such an arrangement facilitates the transportation of devices 50, in particular when they have a considerable length. The roll 52 which is fitted onto a stand 54 also facilitates the lowering and raising of the device 50 into/from a monitoring well 53 or borehole. The flexibility can be achieved by producing the coupling piece 156 in the form of a flexible pipe 157 with a threaded connection 158 at both ends. Alternatively, the coupling piece 156 may comprise a ball joint, which is advantageously hollow, or a cardan joint between two pipe-shaped ends.

Figure 7:
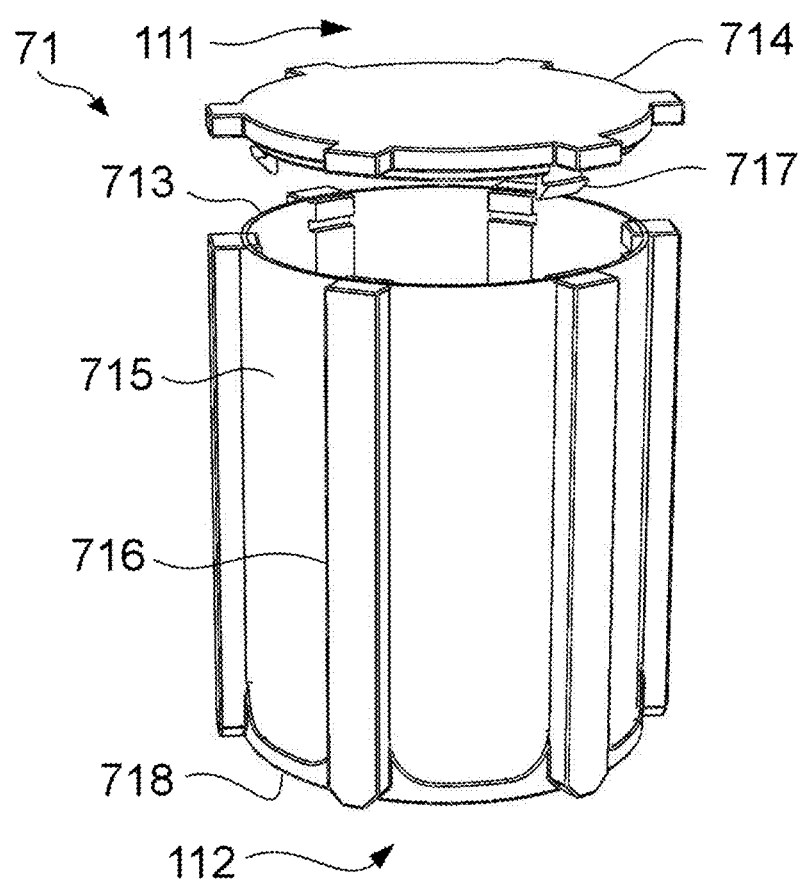
FIG. 7 shows a perspective view of another cartridge according to aspects of the invention.

A cartridge 71 according to an alternative embodiment according to aspects of the invention is illustrated in FIG. 7. Similar to cartridge 11, cartridge 71 comprises a screen 713 which forms an advantageously cylindrical side wall of the cartridge, a bottom plate 718 arranged on a bottom side 112 of the cartridge and a lid 714, arranged on a top side 111 of the cartridge. The screen 713 is permeable to the fluid and may be formed by an advantageously metal net or mesh 715 of appropriate mesh size. The bottom plate 718 and the lid 714 form closures on the bottom side and top side, respectively, of the screen 713 and are impermeable to the fluid. In other words, the fluid can only enter and leave the cartridge 71 via the screen 713.

Reinforcing ribs 716 are advantageously provided along the screen 713 and extend between the bottom plate 718 and the lid 714. The lid 714 and possibly the bottom plate 718 are advantageously detachable, e.g. by means of a click-fit connection 717, which attaches the lid 714 to the cartridge, in particular to the reinforcing ribs 716. A detachable lid has the advantage that the cartridge can be re-used and that it can be emptied and refilled after sampling. Furthermore, these cartridges may be provided with a barcode, thus enabling the identification of both the material composition of the porous matrix and the position in the device.

Figure 8:
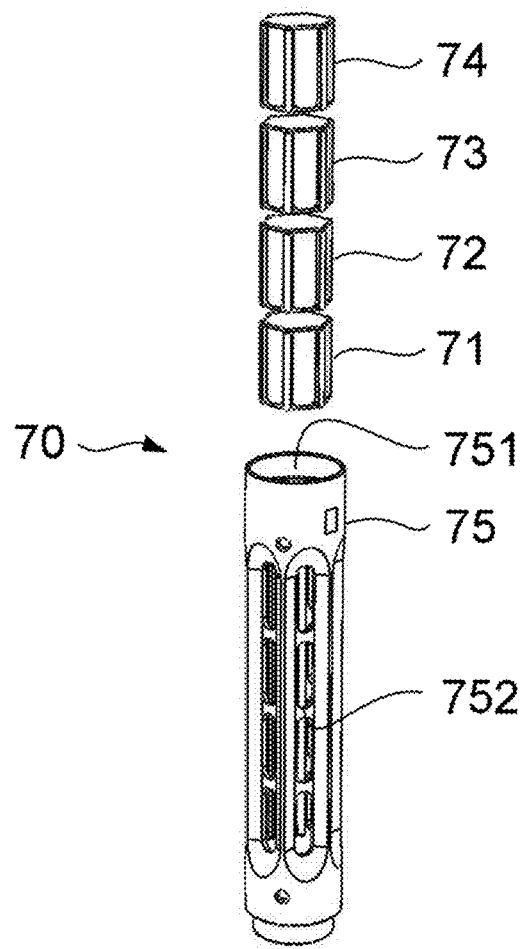
FIG. 8 shows a perspective view of a tube for keeping the cartridges according to FIG. 7 together.

Cartridge 71 differs from cartridges 11-14 by the absence of an axial cavity 117. Referring to FIG. 8, such cartridges 71 are used in devices 70 which comprise a tube 75 designed to receive a plurality of cartridges 71. Tube 75 comprises an axial cavity 751 which is dimensioned such that cartridges 71-74 are arranged one above the other in the cavity 751. Cartridges 71-74 advantageously have the same dimensions. The sleeve of tube 75 is advantageously perforated with flow passage openings 752, which are advantageously arranged at an axial position in correspondence with the position of the cartridges 71-74. Although not illustrated, cartridge 71 may be subdivided into different flow compartments, as described for cartridge 21 (FIG. 13).

Figure 9:
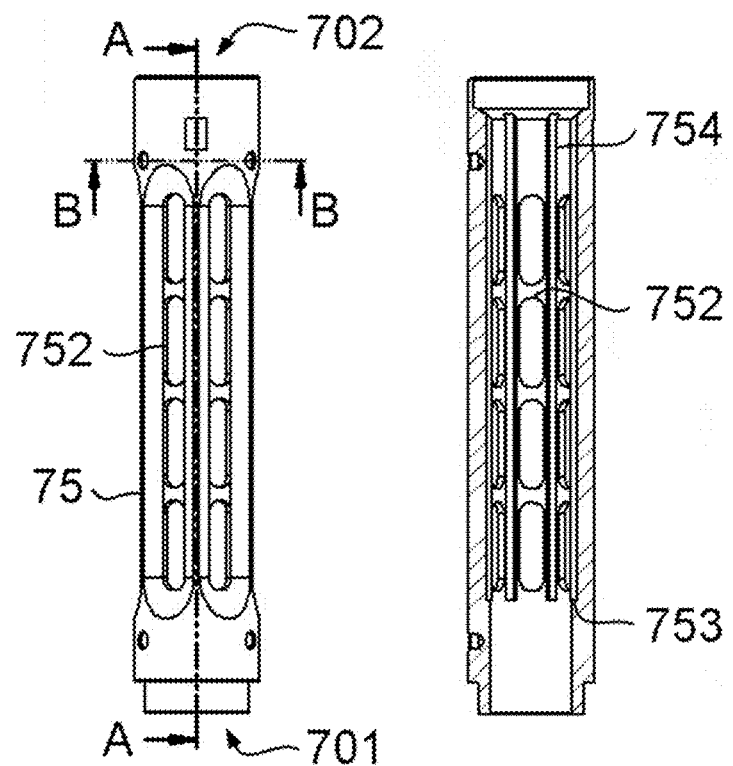
FIG. 9A shows a front view of the tube according to FIG. 8.
FIG. 9B shows a cross-section across section A-A of the tube according to FIG. 9A.
FIG. 9C shows a cross-section across section B-B of the tube according to FIG. 9A.

Referring to FIGS. 9A-C, the tube 75 may internally comprise a stop 753 for the cartridges. The tube 75 is successively loaded with cartridges 71-74 via an opening at a top end 702, wherein the first cartridge 71 reaches stop 753. The stop 753 ensures a correct axial positioning of the cartridges, corresponding to the flow passage openings 752.

Advantageously, the reinforcing ribs 716 form projections which protrude outwards transversely to the screen 713. By providing corresponding grooves 754 in the tube, rotation of the cartridges about the axis of the tube, e.g. caused by the flow of the fluid, is prevented. Possibly, the tube 75 may be provided with a closure (not illustrated) at the top side 702, which prevents the cartridges 71-74 from being able to move axially in the tube.

Figure 10:
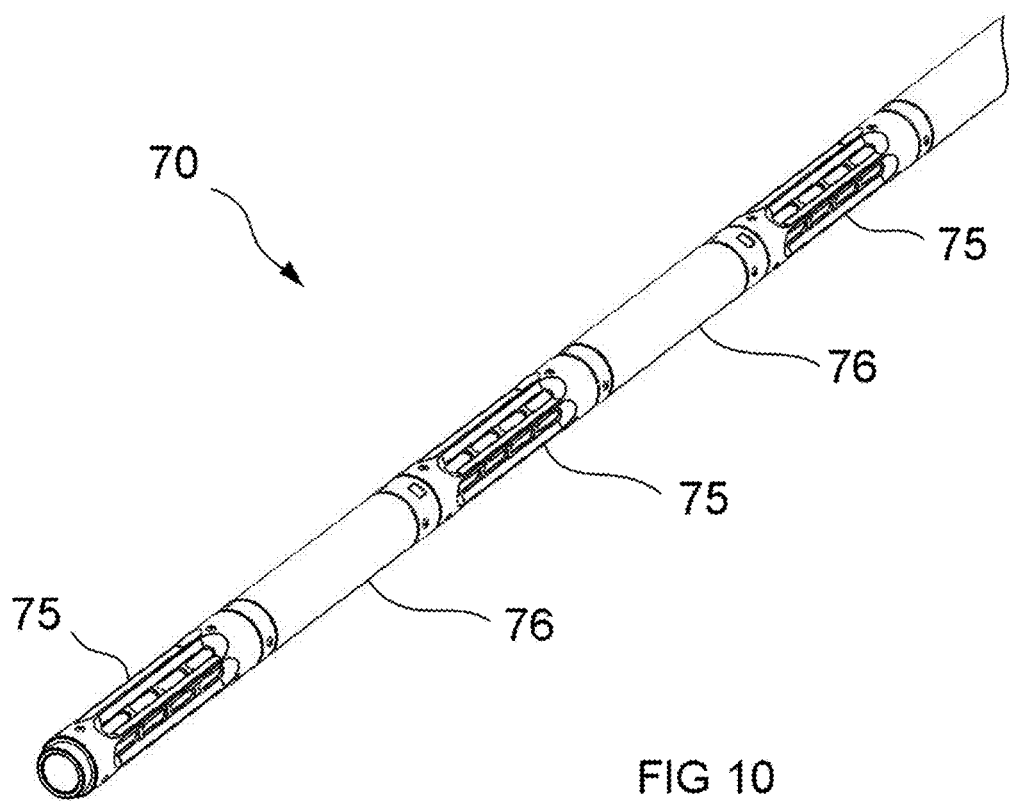
FIG. 10 shows an assembly of the various tubes according to FIG. 9A, which are connected to each other by means of connecting pieces in order to form a tube for sampling.

Both ends 701 and 702 of the tube 75 may be provided with screw thread, by means of which the tube can be attached to connecting pieces and additional tubes, as is illustrated in FIG. 10. Use may be made of connecting pieces 76 of appropriate length to arrange a plurality of tubes 75 at a desired distance from each other. The connecting pieces 76 may be hollow (pipe-shaped) and may be provided with screw thread at the ends, just like the tubes 75. In this way, a division in segments 75 is achieved, similar to the segments 51 of the device 50.

Such devices 70 are particularly suitable for sampling according to the so-called "direct push" technology. With this technique, (hollow) drill rods provided with a drill head are pushed into the ground by a hydraulic hammer, after which a sample is taken. Following sampling, the drill rods are pulled out of the ground. With the "direct push" technology therefore, no pipes remain behind in the ground. It is in this respect that this technology differs from sampling via monitoring well pipes, which remain in the ground permanently. An additional difference is the fact that a monitoring well pipe is arranged in a borehole of a relatively large diameter. The cavity surrounding the monitoring well pipe is usually filled with a granular filter material (e.g. gravel).

The outer diameter of the tubes 75 and the connecting pieces 76 of the devices 70 may be selected such that they fit in the cavity of the drill rods. In such a case, the drill rods and drill head are used to reach the desired depth, following which the device 70 is lowered in the drill rods. The drill rods are then at least partly pulled up, so that the tubes 75 gain access to the groundwater layer. In such a case, the drill head will be a lost drill head, which does not return to the surface when the drill rods are raised. After sampling, both the device 70 and the drill rods which are still underground will be raised using known techniques, e.g. by providing the top of the device 70 with a pull pin.

An alternative "direct push" technique is illustrated in FIGS. 11 and 12. As with the previous method, drill rods 80 provided with a lost drill head 81 are hammered into the ground. A device 70, which may be made from a tube 75 or, if desired, from a series of several tubes, optionally connected via connecting pieces 76, is pushed into the drill rods. At the top, the device comprises engagement means 77 which are provided to cooperate with corresponding engagement means 82 provided on the bottom drill rod. When the drill rods 80 are being raised, the means 82 engage with the means 77, as a result of which the device 70 is pulled up together with the drill rods after sampling. With this arrangement, the device 70 only has to be as long as the length of the section to be measured.

The segments 10, 51 or 75 are preferably designed to receive between 2 and 10, preferably between 2 and 8, preferably between 3 and 6, preferably 4 cartridges 11-14 or 71-74. If fewer parameters are to be measured/determined than the number of cartridges in a segment, dummy cartridges are advantageously used to complete the segment. These dummy cartridges are advantageously filled with an inert granular material, e.g. quartz sand, so that the fluid flow is affected as little as possible. This makes it possible to work with a limited number of standard configurations, so that devices according to the invention are cost-efficient.

Tests have shown that the cartridges advantageously have to have a passage length of at least 20 mm, advantageously at least 25 mm, advantageously at least 30 mm. This means that the diameter of the cartridges advantageously has to be at least 20 mm, advantageously at least 25 mm, advantageously at least 30 mm. However, the diameter is advantageously chosen to be as large as possible, i.e. as the borehole, the drill rod or the monitoring well pipe allow.

The height of the cartridges is advantageously chosen in proportion to the diameter. The ratio between diameter and height of the cartridges is advantageously between 0.5 and 5, advantageously between 1 and 5, advantageously between 2 and 4.

The measuring principle using the cartridges may be described as follows. When a fluid which contains a dissolved substance to be measured flows through the cartridges, the dissolved substance will be adsorbed on the adsorbent which is present in the porous matrix. The accumulation of constituents on the adsorbent during a certain period of time represents the cumulative mass $M_s$ which is collected by the flow chamber. The mass transport may be determined as follows:

$$J = \frac{M_s}{t_d \times A_u}$$

in which $t_d$ is the sampling time or the total time during which the adsorbent remains in the flow field, and $A_u$ is the surface perpendicular to the flow direction which determines the fluid flux in the flow chamber. $A_u$ may be estimated by taking the product of the height and the diameter of the flow chamber of a cartridge.

The streamlines around a borehole or monitoring well pipe are disturbed due to differences in hydraulic conductivity between the groundwater, the filter material around the monitoring well pipe and the measuring system. The water flux (q) through the flow chamber of the cartridge is directly proportional to the water flux ($q_0$) of the groundwater layer according to the equation:

$$q_0 = \frac{q}{\alpha}$$

so that the following holds true for the constituent flux ($J_0$) in the water layer:

$$J_0 = \frac{J}{\alpha}$$

in which $\alpha$ is the convergence/divergence of the flow in the vicinity of the borehole or the monitoring well pipe in which the cartridge is situated. If the cartridge is situated in a monitoring well pipe with surrounding filter material, $\alpha$ may be calculated by means of the following formula:

$$\alpha = \frac{8}{A+B+C+D}$$

in which $$A = \left(1 + \frac{k_A}{k_F}\right)\left(1 + \frac{k_F}{k_S}\right)\left(1 + \frac{k_S}{k_P}\right)$$

$$B = \left(1 - \frac{k_A}{k_F}\right)\left(1 - \frac{k_F}{k_S}\right)\left(1 + \frac{k_S}{k_P}\right)\left(\frac{r_2}{r_3}\right)^2$$

$$C = \left(1 + \frac{k_A}{k_F}\right)\left(1 - \frac{k_F}{k_S}\right)\left(1 - \frac{k_S}{k_P}\right)\left(\frac{r_1}{r_2}\right)^2$$

$$D = \left(1 - \frac{k_A}{k_F}\right)\left(1 + \frac{k_F}{k_S}\right)\left(1 - \frac{k_S}{k_P}\right)\left(\frac{r_1}{r_3}\right)^2$$

with $k_P$, $k_F$, $k_S$ and $k_A$ being the hydraulic conductivity of the flow chamber of the cartridge, the flow screen of the monitoring well pipe, the filter material around the monitoring well pipe and the surrounding groundwater layer, respectively, and $r_1$, $r_2$ and $r_3$ being the radii of the cartridges, the flow screen of the monitoring well pipe and the filter material around the monitoring well pipe, respectively.

In case a tracer is impregnated on a porous matrix, the amount of tracer remaining after a certain period of time is proportional to the amount of fluid which has passed through the flow chamber of the cartridge:

$$M_r = \frac{2}{\pi}[\arcsin\beta - \varepsilon\beta]$$

in which:

$$\beta = \sqrt{1-\varepsilon^2}$$

and $$\varepsilon = \frac{t_d \times q}{2 \times r \times \theta \times R_d}$$

in which $M_r$ is the fraction of remaining tracer compared to its initial mass, r is the radius of the flow chamber of the cartridge, θ is the fluid content of the porous matrix and $R_d$ is the retardation factor of the tracer.

In the case of a tracer which is contained separately in a cartridge and thus has not been impregnated onto the porous matrix, the amount of tracer remaining in the cartridge after a certain time period is proportional to the amount of fluid which has passed through the flow chamber of the cartridge according to the equation:

$$M_r = \gamma \times q$$

in which γ represents the linear ratio factor of leaching, determined under simulated flow conditions.

Figure 14:
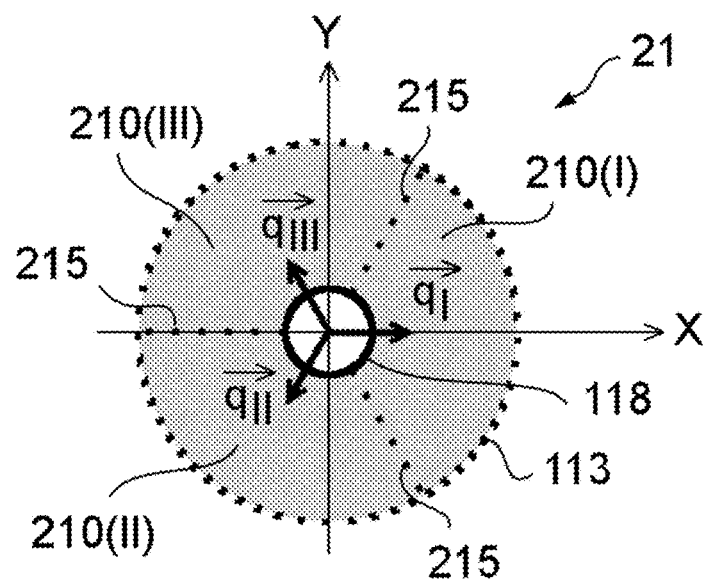
FIG. 14 shows a cross section of the cartridge according to FIG. 13, indicating flux vectors for each flow compartment.

If the flow direction of the fluid is also to be determined by means of the arrangement according to FIG. 13, the following procedure may be followed. It is assumed that the cartridge 21 is subdivided into three equal flow compartments 210(I), 210(II) and 210(III), each of which represents a segment of 120°, all three are filled with adsorbent or tracer which is optionally bound to an adsorbent. A cross section of the arrangement is illustrated in FIG. 14. The orientation which the cartridge 21 had in the fluid is assumed to be known, e.g. by the use of a marker 212, the position/orientation of which with respect to a fixed reference system can be determined. It is assumed that the marker 212 determines the direction of the X axis in FIG. 14. The angle between an external reference (e.g. the magnetic north of a compass) and the X axis is $\alpha_R$.

The horizontal direction of flux may be calculated by means of vector calculation, on the basis of the determination of the fluid flux or pollutant flux through the three flow compartments: $q_I$, $q_{II}$ and $q_{III}$ or, in analogy thereof $J_I$, $J_{II}$ and $J_{III}$. For a groundwater flux, this may be calculated as follows. The vectors $\vec{q}_I$, $\vec{q}_{II}$, and $\vec{q}_{III}$ are added up: $\vec{q} = \vec{q}_I + \vec{q}_{II} + \vec{q}_{III}$. To this end, the x, y components of $\vec{q}$ are first determined:

$$\vec{q}_x = \Sigma_{i=I,II,III} q_i \cdot \cos \alpha_i$$

$$\vec{q}_y = \Sigma_{i=I,II,III} q_i \cdot \sin \alpha_i$$

Subsequently, the direction of the fluid flux in the cartridge can be determined via:

$$\alpha_S = bg \tan(q_y/q_x).$$

This then still has to be corrected for the orientation of the cartridge:

$$\alpha_q = \alpha_S + \alpha_{q'}.$$

Devices according to aspects of the invention are mainly used when measuring underground liquid layers, in particular groundwater layers. However, their application is not limited thereto. In principle, these devices may be used in any flow field of a fluid, e.g. also in surface waters. Neither is the use limited to exclusively vertical arrangements. Devices according to aspects of the invention may also be used in horizontal or diagonal arrangements, e.g. in fault lines in rock slopes. The fluid is not necessarily a liquid, but may also be a gas.

The present invention relates to a device (10) for simultaneously determining a mass transport of a fluid and a mass transport of a substance dissolved in the fluid, comprising at least two cartridges (11-14) filled with a porous matrix, and assembly means (15), configured to keep the cartridges together, characterized in that the top side (111) and the bottom side (112) of each cartridge are non-permeable and the side wall (113) is permeable, and in that the assembly means are configured to keep the cartridges together according to a stack, in which the cartridges may be flowed through in parallel without cross-contamination.

The present disclosure may include one or more of the following concepts:

A. Device (10, 51, 70) for simultaneously determining a mass transport of a fluid and a mass transport of a substance dissolved in the fluid, comprising:
   at least two cartridges (11-14, 71-74), wherein each of the cartridges comprises a top side (111), a bottom side (112) and a side wall (113, 713), wherein the top side, the bottom side and the side wall define a flow chamber,
   assembly means (15, 75) configured to keep the cartridges together, wherein the flow chamber of a first cartridge of the at least two cartridges is filled with a first porous matrix comprising a material composition configured to determine the mass transport of the fluid, and wherein the flow chamber of a second cartridge of the at least two cartridges is filled with a second porous matrix comprising a material composition configured to determine the mass transport of the substance dissolved in the fluid, characterised in that
   the top side (111) and the bottom side (112) of each of the at least two cartridges are non-permeable to the fluid and the side wall (113, 713) of each of the cartridges is permeable for the fluid, and
   the assembly means are configured to keep the cartridges together according to a stack wherein the top side and the bottom side, respectively, of two neighbouring cartridges of the at least two cartridges are opposite one another, such that the flow chambers of the two neighbouring cartridges may be flowed through in parallel without cross-contamination.

B. Device in accordance with paragraph A, wherein the top side and the bottom side, respectively, of the two neighbouring cartridges overlap one another in a projection perpendicular to a face of the top side or the bottom side.

C. Device in accordance with paragraphs A or B, wherein the side wall (113, 713) forms a complete enclosure around the corresponding cartridge.

D. Device in accordance with any of the previous paragraphs, wherein the side wall of each cartridge is cylindrical.

E. Device in accordance with any of the previous paragraphs, wherein the top side and/or the bottom side comprises a non-permeable lid (114, 714), which is detachable.

F. Device in accordance with any of the previous paragraphs, wherein the flow chamber of each of the at least two cartridges is reachable by the fluid via the side wall only.

G. Device in accordance with any of the previous paragraphs, wherein at least one (21) of the at least two cartridges comprises several partitions (215), which are permeable to the fluid and which subdivide the flow chamber (210) into different compartments (I, II, III), wherein each of the compartments is filled with a porous matrix configured to interact with the fluid.

H. Device in accordance with any of the previous paragraphs, wherein at least one (21) of the at least two cartridges comprises means (212) for determining an orientation of the cartridge (21) with respect to an external reference system.

I. Device in accordance with any of the previous paragraphs, wherein each of the at least two cartridges has a diameter greater than or equal to 20 mm.

J. Device in accordance with any of the previous paragraphs, wherein the flow chamber of each of the at least two cartridges has a diameter which is greater than or equal to 20 mm, measured according to an intended flow direction of the fluid.

K. Device in accordance with any of the previous paragraphs, wherein each of the at least two cartridges has a ratio of diameter and height of between 0.5 and 5.

L. Device in accordance with any of the previous paragraphs, wherein each cartridge is provided with a one-dimensional or two-dimensional barcode.

M. Device in accordance with any of the previous paragraphs, wherein the material composition of the first porous matrix and the material composition of the second porous matrix are different.

N. Device in accordance with any of the previous paragraphs, wherein the material composition of the first porous matrix comprises a tracer.

O. Device in accordance with paragraph N, wherein a tracer is absent from the material composition of the second porous matrix.

P. Device in accordance with any of the previous paragraphs, wherein each cartridge comprises a pipe-shaped member (118) which extends through the flow chamber, between the top side (111) and the bottom side (112), in which the pipe-shaped member comprises a wall (118) non-permeable to the fluid, so that the flow chamber is not accessible to the fluid from the pipe-shaped member, and wherein the pipe-shaped member is open at the top side and at the bottom side.

Q. Device in accordance with paragraph P, wherein the assembly means comprise an elongate connecting member (151), configured to be arranged through the pipe-shaped member of each of the at least two cartridges (11-14), and fastening means (152), configured to arrange the at least two cartridges at a fixed axial position with respect to the elongate connecting member.

R. Device in accordance with paragraph Q, which is assembled such that the at least two cartridges are arranged on top of one another, wherein the top side of one (11) of the at least two cartridges and the bottom side of another (12) of the at least two cartridges are opposite one another, so that the at least two cartridges are introduced successively into a borehole or monitoring well.

S. Device in accordance with paragraphs Q or R, wherein the elongate connecting member comprises a rope, in particular a steel rope.

T. Device (10, 51) in accordance with paragraphs Q or R, wherein the elongate connecting member is a bar (151).

U. Device (10, 51) in accordance with paragraph T, wherein the bar is pipe-shaped.

V. Assembly (50), comprising a plurality of devices (51) in accordance with paragraphs T or U, and comprising a flexible coupling (156) configured to connect the bars to each other.

W. Assembly in accordance with paragraph V, wherein the bar (151) of each of the plurality of devices is pipe-shaped, and wherein the flexible coupling (156) is pipe-shaped, such that a continuous fluid passage is created upon assembly of the bars and the flexible coupling.

X. Assembly in accordance with paragraphs V or W, wherein the plurality of devices (51) are assembled using multiple of the flexible couplings to form a segmented sampling device (50) and comprising a roll (52) configured for rolling up the segmented sampling device, wherein the roll has a substantially square cross section, with a side which has a dimension which is substantially equal to the length of one of the plurality of devices.

Y. Device (70) in accordance with paragraphs A to P, wherein the assembly means comprise a tubular housing (75), configured to receive each of the at least two cartridges (71-74), wherein the tubular housing comprises a side wall or sleeve provided with openings (752) through the side wall or sleeve which are in fluid connection with the side wall (713) of the at least two cartridges.

Z. Device in accordance with paragraph Y, wherein the cartridges (71-74) are received in the tubular housing (75) in such a manner that the top side and the bottom side of each of the at least two cartridges are transverse to an axis of the tubular housing.

AA. Device in accordance with paragraphs Y or Z, wherein the assembly means comprise means (753) to arrange the at least two cartridges (71-74) at a fixed position with respect to the openings in the side wall of the tubular housing.

BB. Assembly, comprising a plurality of devices in accordance with any of paragraphs Y to AA, and fastening means configured to rigidly connect the plurality of devices to each other according to an axis of the tubular housing.

CC. Assembly in accordance with paragraph BB, wherein the fastening means comprise an intermediate piece (76), configured to be arranged between two successive devices of the plurality of devices (70).

DD. Assembly in accordance with paragraphs BB or CC, wherein the tubular housing (75) of each of the plurality of devices (70) and optionally the intermediate piece (76) are provided with corresponding screw thread in order to be fastened to each other.

EE. Assembly in accordance with paragraphs BB to DD, comprising a set of drill rods (80) and a drill head (81) configured to be driven into an underground by means of a hydraulic hammer, wherein the tubular housing has an outer diameter which is smaller than or equal to an inner diameter of the set of drill rods.

FF. Method for simultaneously determining a mass transport of a fluid and a mass transport of a substance dissolved in the fluid, comprising:

assembling a device (10, 70) or assembly (50) in accordance with paragraphs, and bringing the at least two cartridges (11-14, 71-74, 21) into contact with the fluid and the dissolved substance, wherein the fluid flows in parallel through the flow chambers of the at least two cartridges.

GG. Method in accordance with paragraph FF, wherein the device or the assembly is lowered vertically into a subsoil, so that the at least two cartridges are arranged one above the other.

The invention claimed is:

1. A device (10, 51, 70) for simultaneously determining a mass transport of a fluid and a mass transport of a substance dissolved in the fluid, comprising:

at least two cartridges (11-14, 71-74), wherein each of the cartridges comprises a top side (111), a bottom side (112) and a side wall (113, 713), wherein the top side, the bottom side and the side wall define a flow chamber, assembly means (15, 75) configured to keep the cartridges together, wherein the flow chamber of a first cartridge of the at least two cartridges is filled with a first porous matrix comprising a material composition configured to determine the mass transport of the fluid, and wherein the flow chamber of a second cartridge of the at least two cartridges is filled with a second porous matrix comprising a material composition configured to determine the mass transport of the substance dissolved in the fluid, wherein:

the top side (111) and the bottom side (112) of each of the at least two cartridges are non-permeable to the fluid and the side wall (113, 713) of each of the cartridges is permeable for the fluid, the assembly means are configured to keep the cartridges together according to a stack wherein the top side and the bottom side, respectively, of two neighbouring cartridges of the at least two cartridges are opposite one another, such that the flow chambers of the two neighbouring cartridges may be flowed through in parallel without cross-contamination, and the side wall (113, 713) forms a complete enclosure around the corresponding cartridge;

wherein the top side and/or the bottom side comprises a non-permeable lid (114, 714), which is detachable.

2. The device according to claim 1, wherein the top side and the bottom side, respectively, of the two neighbouring cartridges overlap one another in a projection perpendicular to a face of the top side or the bottom side.

3. The device according to claim 1, wherein the flow chamber of each of the at least two cartridges is reachable by the fluid via the side wall only.

4. The device according to claim 1, wherein the material composition of the first porous matrix and the material composition of the second porous matrix are different.

5. The device according to claim 1, wherein the material composition of the first porous matrix comprises a tracer.

6. The device according to claim 5, wherein a tracer is absent from the material composition of the second porous matrix.

7. A method for simultaneously determining a mass transport of a fluid and a mass transport of a substance dissolved in the fluid, comprising:

assembling the device of claim 1, and bringing the at least two cartridges (11-14, 71-74, 21) into contact with the fluid and the dissolved substance, wherein the fluid flows in parallel through the flow chambers of the at least two cartridges.

8. The method of claim 7, wherein the device or the assembly is lowered vertically into a subsoil, wherein the at least two cartridges are arranged one above the other.

9. A device (10, 51, 70) for simultaneously determining a mass transport of a fluid and a mass transport of a substance dissolved in the fluid, comprising:

at least two cartridges (11-14, 71-74), wherein each of the cartridges comprises a top side (111), a bottom side (112) and a side wall (113, 713), wherein the top side, the bottom side and the side wall define a flow chamber, assembly means (15, 75) configured to keep the cartridges together, wherein the flow chamber of a first cartridge of the at least two cartridges is filled with a first porous matrix comprising a material composition configured to determine the mass transport of the fluid, and wherein the flow chamber of a second cartridge of the at least two cartridges is filled with a second porous matrix comprising a material composition configured to determine the mass transport of the substance dissolved in the fluid, wherein:

the top side (111) and the bottom side (112) of each of the at least two cartridges are non-permeable to the fluid and the side wall (113, 713) of each of the cartridges is permeable for the fluid, the assembly means are configured to keep the cartridges together according to a stack wherein the top side and the bottom side, respectively, of two neighbouring cartridges of the at least two cartridges are opposite one another, such that the flow chambers of the two neighbouring cartridges may be flowed through in parallel without cross-contamination, and the side wall (113, 713) forms a complete enclosure around the corresponding cartridge, wherein at least one (21) of the at least two cartridges comprises several partitions (215), which are permeable to the fluid and which subdivide the flow chamber (210) into different compartments (I, II, III), wherein each of the compartments is filled with a porous matrix configured to interact with the fluid.

10. The device according to claim 9, wherein each of the at least two cartridges has a ratio of diameter and height of between 0.5 and 5.

11. The device according to claim 9, wherein the material composition of the first porous matrix and the material composition of the second porous matrix are different.

12. The device according to claim 9, wherein the material composition of the first porous matrix comprises a tracer, wherein a tracer is absent from the material composition of the second porous matrix.

13. A device (10, 51, 70) for simultaneously determining a mass transport of a fluid and a mass transport of a substance dissolved in the fluid, comprising:

at least two cartridges (11-14, 71-74), wherein each of the cartridges comprises a top side (111), a bottom side (112) and a side wall (113, 713), wherein the top side, the bottom side and the side wall define a flow chamber, assembly means (15, 75) configured to keep the cartridges together, wherein the flow chamber of a first cartridge of the at least two cartridges is filled with a first porous matrix comprising a material composition configured to determine the mass transport of the fluid, and wherein the flow chamber of a second cartridge of the at least two cartridges is filled with a second porous matrix comprising a material composition configured to determine the mass transport of the substance dissolved in the fluid, wherein:

the top side (111) and the bottom side (112) of each of the at least two cartridges are non-permeable to the fluid and the side wall (113, 713) of each of the cartridges is permeable for the fluid, the assembly means are configured to keep the cartridges together according to a stack wherein the top side and the bottom side, respectively, of two neighbouring cartridges of the at least two cartridges are opposite one another, such that the flow chambers of the two neighbouring cartridges may be flowed through in parallel without cross-contamination, and the side wall (113, 713) forms a complete enclosure around the corresponding cartridge, wherein each cartridge is provided with a one-dimensional or two-dimensional barcode.

14. A device (10, 51, 70) for simultaneously determining a mass transport of a fluid and a mass transport of a substance dissolved in the fluid, comprising:

at least two cartridges (11-14, 71-74), wherein each of the cartridges comprises a top side (111), a bottom side (112) and a side wall (113, 713), wherein the top side, the bottom side and the side wall define a flow chamber, assembly means (15, 75) configured to keep the cartridges together, wherein the flow chamber of a first cartridge of the at least two cartridges is filled with a first porous matrix comprising a material composition configured to determine the mass transport of the fluid, and wherein the flow chamber of a second cartridge of the at least two cartridges is filled with a second porous matrix comprising a material composition configured to determine the mass transport of the substance dissolved in the fluid,
wherein:
the top side (111) and the bottom side (112) of each of the at least two cartridges are non-permeable to the fluid and the side wall (113, 713) of each of the cartridges is permeable for the fluid,
the assembly means are configured to keep the cartridges together according to a stack wherein the top side and the bottom side, respectively, of two neighbouring cartridges of the at least two cartridges are opposite one another, such that the flow chambers of the two neighbouring cartridges may be flowed through in parallel without cross-contamination, and
the side wall (113, 713) forms a complete enclosure around the corresponding cartridge,
wherein each cartridge comprises a pipe-shaped member (118) which extends through the flow chamber, between the top side (111) and the bottom side (112), in which the pipe-shaped member comprises a wall (118) non-permeable to the fluid, wherein the flow chamber is not accessible to the fluid from the pipe-shaped member, and wherein the pipe-shaped member is open at the top side and at the bottom side.

15. The device according to claim 14, wherein the assembly means comprise an elongate connecting member (151), configured to be arranged through the pipe-shaped member of each of the at least two cartridges (11-14), and fastening means (152), configured to arrange the at least two cartridges at a fixed axial position with respect to the elongate connecting member.

16. The device according to claim 15, wherein the elongate connecting member comprises a rope, in particular a steel rope.

17. The device according to claim 15, wherein the elongate connecting member is a bar (151).

18. The device according to claim 17, wherein the bar is pipe-shaped.

19. An assembly, comprising a plurality of devices (51) according to claim 17, and further comprising a flexible coupling (156) configured to connect the bars to each other.

20. The assembly according to claim 19, wherein the bar (151) of each of the plurality of devices is pipe-shaped, and wherein the flexible coupling (156) is pipe-shaped, wherein a continuous fluid passage is created through the bars and the flexible coupling.

21. The assembly according to claim 19, wherein the plurality of devices (51) are assembled using multiple of the flexible couplings to form a segmented sampling device (50) and comprising a roll (52) configured for rolling up the segmented sampling device, wherein the roll has a substantially square cross section, with a side which has a dimension which is substantially equal to the length of one of the plurality of devices.

* * * * *